United States Patent [19]

Thornton et al.

[11] 4,014,216
[45] Mar. 29, 1977

[54] APPARATUS FOR SAMPLING GAS MIXTURES

[76] Inventors: Joseph Scott Thornton, 5902 W. Bee Caves Road, Austin, Tex. 78746; Edward Dale Golla, 5112 N. Lamar Blvd., Austin, Tex. 78751

[22] Filed: Mar. 22, 1976

[21] Appl. No.: 669,121

[52] U.S. Cl. .............................. 73/421.5 R; 73/28
[51] Int. Cl.² .......................................... G01N 1/22
[58] Field of Search ............ 73/421.5 R, 422 R, 28

[56] References Cited

UNITED STATES PATENTS

| 2,481,882 | 9/1949 | Sebald | 73/422 R |
| 3,010,583 | 11/1961 | Kenyon | 73/422 R |
| 3,966,439 | 6/1976 | Lysander | 73/421.5 R |

FOREIGN PATENTS OR APPLICATIONS

| 86,749 | 4/1959 | Denmark | 73/422 R |

*Primary Examiner*—S. Clement Swisher
*Attorney, Agent, or Firm*—Lawrence I. Field

[57] ABSTRACT

A light weight apparatus for sampling a gas mixture, especially a gas under pressure, in order to ascertain the extent of contamination in said mixture, including gaseous, liquid and solid contaminants. The apparatus includes in combination a filter means to capture a sample of the solid particulates and the vapor and a means to capture a representative sample of pressurized gas. A novel fitting in which two hypodermic needles are embedded is operatively connected to the pressurized gas at one of its ends and to a sampling tube at the other of its ends. A modified fitting is used to obtain a sample of the ambient atmosphere if this is desired.

9 Claims, 6 Drawing Figures

APPARATUS FOR SAMPLING GAS MIXTURES

This invention relates to an apparatus for sampling a gas mixture such as the gas delivered by a compressor, for the purpose of ascertaining the presence of contaminants in said gas mixture.

Air or oxygen-enriched gas mixtures under pressure are utilized by persons working underwater, for example scuba divers, or hard hat deep sea divers, and by other working in special environments, such as fire fighters or mountain climbers. Contaminants in the gas supplied to such persons for breathing can produce fatigue, dizziness and confusion, which can cause serious accidents and even death. The plight of the underwater diver is especially serious since he must receive air at super-atmospheric pressures depending on the depth to which he is diving, and the physiological effects of contaminants are greatly increased by pressure. Most city dwellers could survive a level of air pollution on the surface of the earth that would be fatal to most divers at a depth of 150 feet. Since many contaminants are odorless, the diver, mountain climber, or other persons to whom the gas is furnished for breathing, may be unaware of the presence of the contaminant until his life is in serious danger, at which time he may not be able to take steps about it since he is completely dependent on the furnished gas for survival in his environment.

The gases supplied for breathing are commonly stored in cylinders under pressure and are charged into such storage containers by means of a compressor, or the breathing gas mixture is supplied directly to the user by means of a hose from a compressor. In some instances, possibly owing to wear of the compressor parts, hydrocarbons, carbon monoxide, oil mist, rush and other solid particles are included in the gas furnished by the compressor. In other cases, as in air compressors located in regions of high air pollution levels, the contaminants can be present in the gas before it is compressed. The present invention provides sampling devices adapted to facilitate the detection of such contaminants, whereby a potential contamination problem from a compressor which is sampled regularly can be corrected by preventative maintenance, before the level of contamination reaches proportions which would be dangerous to persons using the compressed gas discharged by the compressor.

Previous methods of taking gas samples from compressors have required the use of heavy, bulky and expensive equipment. Furthermore, most of the equipment available has not provided a means for taking a correct sample of airborne particulates at the time the gas sample is taken. The most common procedure for taking a gas and particulate sample from compressors has been to fill a thick walled metal high-pressure flask directly from the compressor output. The analytical laboratory employed for determining the contaminant levels has no problem with the gas part of the analysis because gases will be homogeneously mixed. However, accurate analysis of the particulate part of the sample has been an insurmountable problem for all practical purposes. Liquid droplets (vapors) will condense on the inside of the flask and the solid particles may or may not come out of the flask. The analytical laboratory can bleed the gas out of the flask through a tared filter in hopes of capturing a particulate sample, but little confidence can be placed in the result.

The most advanced sampling systems available up until the time of this invention have been described recently in the Proceeding of the 1973 Divers Gas Purity Symposium, Nov. 27 and 28, Columbus, Ohio. If these systems were available, they would enable one to obtain correct particulate samples. However, they are infrequently used because they suffer from a number of practical disadvantages. The principal disadvantages are the expense and weight of the equipment and the fact that the gas sample is taken under pressure. These disadvantages, individually and in combination, create, as a minimum, a financial hardship on the individual or organization using the equipment, and in the extreme case, prevent an accurate sample from being shipped to a laboratory for analysis. The United States Postal Service will not accept pressurized gases, and air freight carriers reserve the right to depressurize any container they handle. Consequently, surface or water transportation are the only reliable means of sending pressurized samples to a laboratory, and this is inconvenient and time consuming unless a laboratory is located close by. The depressurizaton of the sample container to permit it to be shipped is possible, but can lead to further problems if not performed by a skilled technician. For example, if gas flow is permitted to pass through the filter in the wrong direction, the filter can be damaged or a portion of the particulate matter captured on the filter can be lost. The bulk and weight of the equipment used in the past has made transportation costs prohibitive in many instances. The present invention overcomes these disadvantages because it provides a light-weight, inexpensive sampling system which can be shipped anywhere in the world by air for a modest cost. Furthermore, since the gas sample is taken at low pressure, there are no restrictions as to modes of transportation available. Thus the person desiring his compressor output to be analyzed is no longer helpless if a local laboratory is not available, or captive to the price charged if a local laboratory is available.

Previous portable means for taking atmospheric air samples have similarly required bulky and/or unnecessarily expensive equipment. Common techniques include filling a plastic bag using a portable diaphragm pump, filling a large gas syringe, and filling a partially evacuated metal can as described in U.S. Pat. No. 3,618,393 issued Nov. 9, 1971. The gas filled bag is reusable, but has a severely limited service life because some gases can preferentially diffuse through the membrane. Furthermore, the bag is bulky. The types of gas tight syringes suitable for air sampling are very expensive. The partially evacuated metal can is not reusable since the process of removing the sample requires puncturing the can. Thus, if for some reason the gas sample taken was not considered adequate, there would be no practical means of replacing the original sample taken in the can with an adequate sample.

The principal object of this invention is to provide an improved air sampling system to facilitate the analysis of impurities in the compressed air used for breathing, or other gases, especially gases under pressure.

A further object of the invention is to provide a means for separately analyzing particulate, vapor, and gaseous contaminants in compressed gases provided for breathing.

Still another object of this invention is to provide a better means for sampling gases at atmospheric or subatmospheric pressure for various purposes. For example, taking an air sample at the intake of an air compressor can help determine if contaminants found in the compressor output are due to the compressor itself or to high ambient levels of contaminaton.

These, and other objectives of the invention will be apparent to those skilled in the art from the description which follows, taken in conjunction with the drawings in which.

Figure 1:
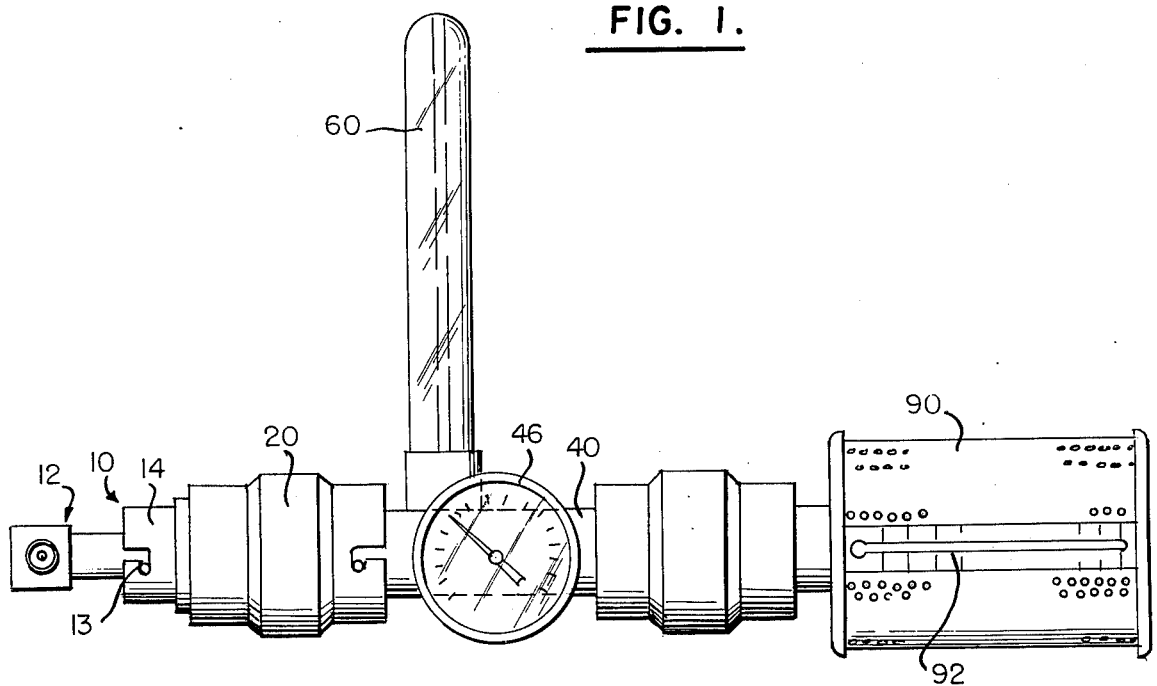
FIG. 1 is a view in perspective of a system used for compressed air sampling showing a preferred embodiment of this invention.

As best seen in FIG. 1, the sampling apparatus 10 includes a filter section 20, a flow measuring section 40 and a sample container 60. To analyze for gaseous impurities such as CO, $CO_2$, $CH_4$, or other hydrocarbon gases, it is merely necessary to capture a representative sample of the gas in a suitable container. However, in order to analyze for condensable vapors and solid particulate matter, the capture of a representative sample is not such a simple matter because the particulates are not distributed uniformly, either temporally or spatially in the gas stream.

For the purposes of illustration, FIG. 1 shows a scuba style inlet fitting 12 for connection with the compressed air supply (not shown) to be sampled. The inlet fitting 12 may be inserted into one end of a bushing 14 by means of a twist lock connection 13. A shoulder 15 is provided on the surface of bushing 14 to receive a filter device 20 shown in greater detail in FIG. 2.

Figure 2:
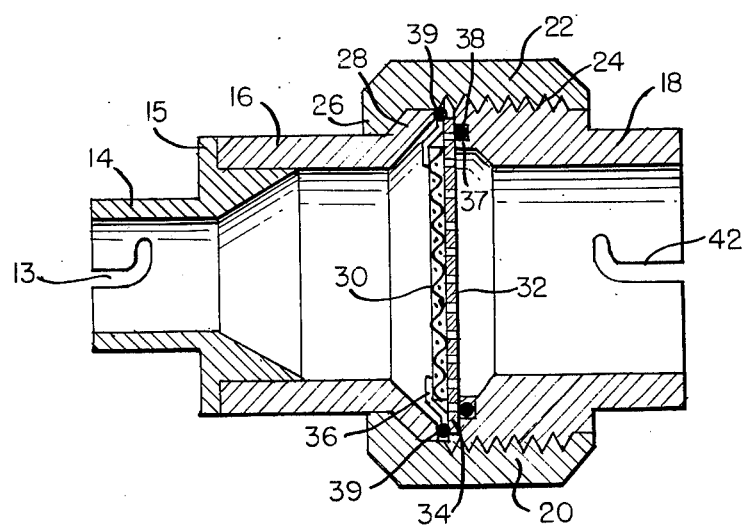
FIG. 2 is an enlarged view, partly in section, of the filter section of the system of FIG. 1.

The filter device 20 shown in FIG. 2 includes an inlet pipe 16 and an outlet pipe 18, coupled by a union 22. Coupling is achieved by means of screw threads 24 on outlet pipe 18 and by a collar 26 adapted to bear against a shoulder 28 flaring outwardly at the exit end of inlet pipe 16. Clamped between the shoulder 28 and the threaded end of outlet pipe 18 are a fiberglass mesh filter 30 and a perforated disc 32. Disc 32 is positioned behind filter 30 and supports filter 30 and permits the gas and vapor admitted by inlet pipe 16 to pass into outlet pipe 18, while any solid or liquid (vapor) particulates in the entering gas are collected on fiberglass filter 30. Perforated disc 32 includes an annular rim 34 from which a plurality of small metal tangs 36 are provided which act as a means for centering filter 30 in the passageway of filter section 20. Packing such as an "O" ring 37 or outer gasket is inserted in groove 38 provided in the end face of pipe 18. Another gasket 39 is provided between the face of pipe 16 and the solid annular rim 34 of disc 32. The gaskets 37 and 39 prevent gas from passing around the filter 30. Pipe 18 is provided with a slot 42 for a twist-lock attachment to the flow section 40 of the apparatus, to which filter section 20 is connected.

In order to quantitatively analyze for solid and liquid (condensable vapors) particulate matter, it is necessary to collect this matter on filter 30 and while doing so, to determine the volume of gas passing through the filter 30. Determination of the volume of gas is accomplished in the flow measuring section 40 of the apparatus of this invention, seen in FIG. 3 and 4.

Figure 4:
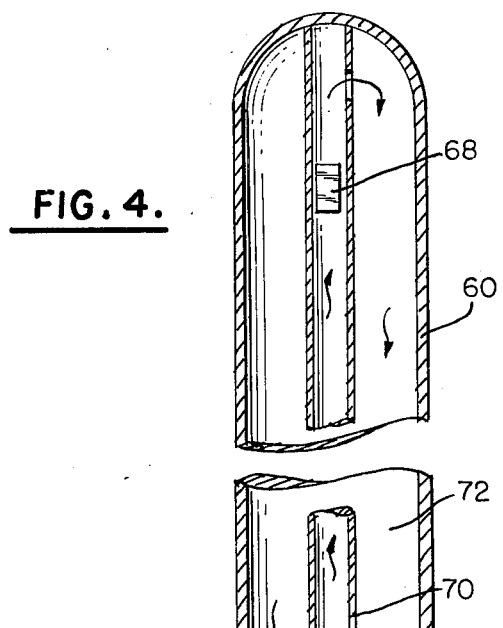
FIG. 4 is an enlarged view, partly in section, of an air transfer fitting and sample tube used with the system of FIG. 1.

The flow measuring section 40 includes a short length of pipe 43 which may be made of synthetic resin polymer or of suitable light weight metal such as aluminum. An air sampling tube 60 and a pressure gauge 46 are operatively connected to pipe 43 and to the gas flowing through pipe 43 by means of threaded fittings. In FIG. 4, which shows the air transfer fitting 44 and gas sample tube 60 in greater detail, the air transfer fitting 44 has a threaded base 45 which screws into pipe 43, and a cup-shaped upper end 48 adapted to receive the gas sample tube 60 onto which a sampling cap 50 has been screwed by means of the threads 52.

Figure 5:
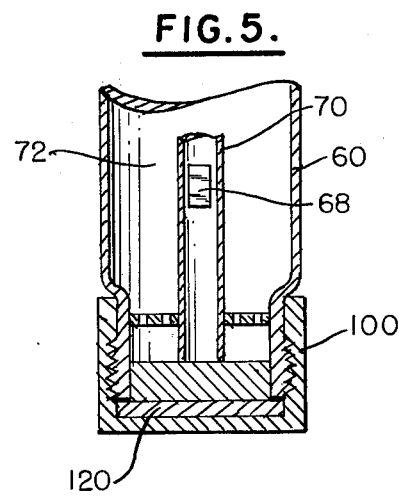
FIG. 5 is an enlarged view of the sample tube of FIG. 4 with the shipping/storage cap in place.

As shown in FIG. 4, the air sample tube 60 is closed at its open end by a rubber septum 58 which fits tightly into the open end of tube 60 and which is prevented from being expelled by internal pressure in tube 60 by the collar 54 on sampling cap 50. Two hypodermic needles 62, 64 permanently embedded in and extending through fitting 44, penetrate the end of the sample tube 60 through the septum 58 at the open end of the tube when tube 60 is pushed into cup 48. The compression in rubber septum 58 effects a gas tight seal around the two needles 62, 64. The center needle 62 allows air from the flow section 43 to enter the center chamber 70 of the sample tube 60 and the off-center needle 64 permits air from the outer chamber 72 of the sample tube 60 to vent to the atmosphere through a side vent 74 in needle 64. Air flow from section 43 into the needle 64 is prevented by plug 65. In order to avoid inadvertent over pressurization of the sample bottle, which will cause the septum to pop out of the end of the bottle, needle 64 is commonly made larger in inside diameter than needle 62. This insures that the pressure in the bottle is always less than the pressure inside pipe 43. During the taking of an air sample, air is permitted to flow through the tube a sufficient length of time to completely purge the tube of its previous contents. The inner chamber 70 of the sample tube 60 is equipped with a float 68 to indicate that a sample is being taken, i.e., that the needles are not clogged. The sample tube can be "calibrated" so that the lifting of the float means that the sample tube will be 99.99% purged in a specific period of time(say, 1 minute). After purging, the sample tube is removed from the air transfer connector and the sampling cap 50 is replaced by a solid cap 100 with a special metal foil liner 120 shown in FIG. 5. The liner 120 prevents escape of the contents of tube 60 by diffusion of gases through the rubber septum by effecting a tight seal between tube 60 and liner 120.

Figure 3:
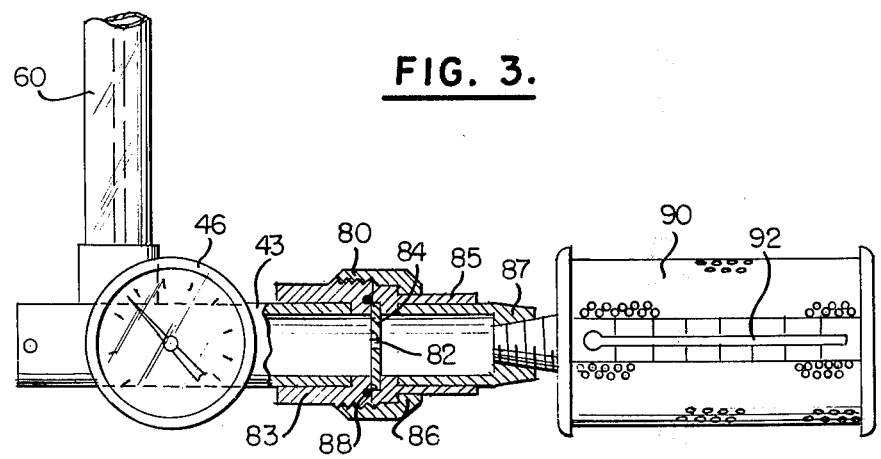
FIG. 3 is an enlarged view, partly in section, of the flow measuring section of the system of FIG. 1.

The means for measuring the flow rate of the gas stream and the means for providing sufficient pressure inside pipe 43 to force the purging of the sample tube 60 via needles 62 and 64 are provided by the orifice plate 84 shown in FIG. 3. Orifice plate 84 is supported between the inlet 83 and outlet 85 pieces of union 80. A gasket 88 prevents gas from escaping union 80 except through orifice 82 in orifice plate 84. The size of orifice opening 82, the pressure reading on the gauge 46, and the temperature of the exhaust gas as measured on a thermometer 92 are sufficient to define the volume rate of flow of gas through the apparatus. A muffler 90 is provided to reduce the noise created by the gas rushing through orifice opening 82.

Figure 6:
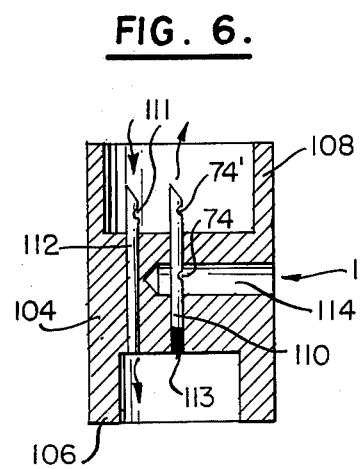
FIG. 6 is a view, partly in section, of an air transfer fitting which can be used in conjunction with the sample tube of FIG. 5 and an external source of vacuum (such as a rubber bulb type vacuum pump) to obtain a sample of gas at atmospheric or subatmospheric pressure.

FIG. 6 shows a modification 104 of the air transfer fitting 44 of FIG. 4 which can be used for taking samples of gas at atmospheric pressure or below. A sample tube 60 with sampling cap 50 attached is pressed into the cup end 108 of fitting 104, and when a source of vacuum such as a rubber bulb type hand operated vacuum pump (not shown) is connected to the other end 106 of the fitting 104 then a sample of gas can be taken into the tube. The vacuum pulls gas from the sample tube 60 via the side vent 111 and end opening in needle 112 thereby causing new sample gas to enter the tube 60 via chamber 114 and the two side openings 74, 74' in needle 110. Plug 113 prevents air from short-circuiting the sample bottle. The pressure of the gas entering chamber 114 can be very low but not lower than the vacuum provided at the chamber 106.

It is believed that the use of the apparatus will be clear from the preceding description, but in order to complete this specification, such a description follows:

The shipping cap is unscrewed from one of the sampling bottles, and the sampling cap is screwed on.

After the male end of the flow section has been inserted into the large opening on the filter union, the pin is lined up with the slots, the filter union and the flow section are pressed firmly together and twisted to lock the two sections together. Then the scuba input fitting is inserted into the filter union and twisted to lock in place.

The collection of the particulate sample on the filter in the filter union is a timed (3 minute) procedure. While the particulate sample is being collected, an air sample is also taken, but in a shorter length of time (about 30 seconds). The particulate sample and the air sample are taken within the same 3 minute time span.

The air flow is carefully started through the sampling system, using the valve in the air supply system to control the flow rate. The flow is increased until the gauge in the flow section is stabilized at some convenient value, which is maintained during the complete test which is 3 minutes.

About half way through the 3 minute sampling interval the cap end of the sample bottle is pressed straight into the air transfer connector being careful to avoid any twisting which might damage the needles. The white float should have risen inside the sample bottle. The bottle is left in place for at least 30 seconds to insure that a representative air sample has been taken. After the air sample has been obtained, the bottle is removed from the air transfer connector, the sampling cap is removed and the shipping cap is replaced while the air is still flowing through the system.

When the 3 minutes for taking the particulate sample have passed, the air supply is shut off, the final temperature is recorded and the system is disassembled.

An ambient air sample is taken by placing the sampling cap on another bottle and inserting the bottle into the ambient air transfer fitting. Aiming the small intake hole of the ambient air transfer fitting as close as possible to the air intake to the compressor, the bulb is pumped 8–10 times. After the sample is taken the sampling cap is removed, and the shipping cap is replaced (finger tight).

We claim:

1. A sampling system for taking gas samples, vapor and solid particulates therein which includes in combination:
    a gas sample container;
    means to connect said sample container with a pressurized source of gas to be analyzed;
    a filter section operatively connected to said pressurized gas;
    a flow measuring section operatively connected to said pressurized gas; and
    means connecting the sample container to the rest of the system, said means comprising a plug adapted to connect to said pressurized gas and having a minute passage through which gas to be sampled can flow into said sample container.

2. The combination of claim 1 which includes a fitting operatively connected with said tube, said fitting having a cup-shaped upper end adapted to receive said gas sample container.

3. The combination of claim 2 wherein the fitting is connected to said container by means of a threaded connection.

4. The combination of claim 2 wherein the fitting includes two hypodermic needles, each of said needles having a tubular bore extending the length of the needle, one of said needles extending from an entry end of said fitting and through said fitting terminating beyond the discharge end of said fitting, the other of said needles extending beyond the discharge end of said fitting to a discharge port in said fitting.

5. The combination of claim 2 wherein the sample container includes an open end adapted to be operatively connected to said cup-shaped upper end;
    a closed end opposite said open end;
    a plug positioned across the open end of said sampling tube and constructed of material which is easily pierced by a hypodermic needle; and
    means to hold said plug in place across the open end of said sampling tube.

6. The combination of claim 5 wherein the sampling tube includes a center chamber defined by a tube extending between the closed end and the open end.

7. A fitting having one end of said fitting adapted to cooperate with a gas pumping device and a cup-shaped recess at the opposite end of said fitting adapted to receive a sampling container and two hypodermic needles embedded in said fitting with one end of each of said needles extending into said cup-shaped recess, one of said hypodermic needles also opening into the opposite end of said fitting and the other of said hypodermic needles opening to the side of said fitting.

8. A fitting comprising a plug having a lower end adapted to cooperate with a source of gas to be sampled:
    a cup-shaped upper end adapted to receive a sampling container;
    two hypodermic needles, one passing through said plug and extending into said cup-shaped end, the other of said needles extending into said cup-shaped end, venting before the entry end of said plug; and
    a traverse bore in said fitting operatively connected to said vent.

9. The apparatus of claim 1 in which the filter includes:
    at least one mesh filter disposed transversely of a passage through which the gas to be sampled is passed;
    a perforated disc positioned behind said filter and adapted to support said mesh filter, said perforated disc including an annular run from which tangs project to engage the mesh filter and enter the same.

* * * * *